(12) United States Patent
Nakano et al.

(10) Patent No.: US 10,077,425 B2
(45) Date of Patent: Sep. 18, 2018

(54) METHOD FOR PRODUCING CILIARY MARGINAL ZONE-LIKE STRUCTURE

(71) Applicants: SUMITOMO CHEMICAL COMPANY, LIMITED, Tokyo (JP); RIKEN, Wako-shi, Saitama (JP); Miyuki Sasai, Kobe (JP)

(72) Inventors: Tokushige Nakano, Osaka (JP); Satoshi Ando, Osaka (JP); Yoshiki Sasai, Wako (JP); Mototsugu Eiraku, Wako (JP)

(73) Assignees: SUMITOMO CHEMICAL COMPANY, LIMITED, Tokyo (JP); RIKEN, Wako (JP)

( * ) Notice: Subject to any disclaimer, the term of this patent is extended or adjusted under 35 U.S.C. 154(b) by 0 days.

(21) Appl. No.: 14/406,440

(22) PCT Filed: Jun. 7, 2013

(86) PCT No.: PCT/JP2013/065878
§ 371 (c)(1),
(2) Date: Dec. 8, 2014

(87) PCT Pub. No.: WO2013/183774
PCT Pub. Date: Dec. 12, 2013

(65) Prior Publication Data
US 2015/0132787 A1 May 14, 2015

(30) Foreign Application Priority Data

Jun. 8, 2012 (JP) .................................. 2012-130521

(51) Int. Cl.
*C12N 5/079* (2010.01)
*A61L 27/36* (2006.01)
*A61L 27/38* (2006.01)
*A61K 35/30* (2015.01)

(52) U.S. Cl.
CPC ............ *C12N 5/0621* (2013.01); *A61K 35/30* (2013.01); *A61L 27/3604* (2013.01); *A61L 27/3895* (2013.01); *C12N 2500/90* (2013.01); *C12N 2501/41* (2013.01); *C12N 2501/415* (2013.01); *C12N 2501/727* (2013.01); *C12N 2506/02* (2013.01); *C12N 2506/08* (2013.01)

(58) Field of Classification Search
CPC .............. C12N 5/0621; C12N 2506/08; C12N 2501/41; C12N 2501/727; C12N 2501/415; C12N 2500/90; C12N 2506/02; A61L 27/3895; A61L 27/3604; A61K 35/30
See application file for complete search history.

(56) References Cited

U.S. PATENT DOCUMENTS

2006/0122111 A1  6/2006  Furukawa
2013/0040330 A1  2/2013  Sasai et al.
2014/0341864 A1  11/2014  Nakano et al.

FOREIGN PATENT DOCUMENTS

WO      WO 2011/055855 A1      5/2011

OTHER PUBLICATIONS

Kuwahara et al. Generation of a ciliary margin-like stem cell niche from self-organizing human retinal tissue. Nat Commun. Feb. 19, 2015;6:6286 p. 1-15.*
Wei et al., *Journal of Third Military Medical University*, 25(24): 2161-2164 (Dec. 2003).
Chinese Patent Office, First Office Action in Chinese Patent Application No. 201380041868 (dated Jan. 15, 2016).
Stephens et al., *Developmental Dynamics*, 239: 2066-2077 (2010).
Kubo et al., *Development*, 136: 1823-1833 (2009).
Denayer et al., *Stem Cells*, 26: 2063-2074 (2008).
Eiraku et al., *BioEssays*, 34: 17-25 (2012).
Eiraku et al., *Nature*, 472: 51-56 (2011).
Fuhrmann, Sabine, *Organogenesis*, 4: 60-67 (2008).
Kubo et al., *Development*, 130: 587-598 (2003).
Nakano et al., *Cell Stem Cell*, 10: 771-785 (2012).
Seiler et al., *European Journal of Neuroscience*, 31(3): 508-520 (2010).
Vugler et al., *Mechanisms of Development*, 124(11-12): 807-829 (2007).
European Patent Office, Extended European Search Report in European Patent Application No. 13800106.0 (dated Nov. 19, 2015).
Japanese Patent Office, International Search Report in International Patent Application No. PCT/JP2013/065878 (dated Jul. 30, 2013).
Phllips et al., "Blood-Derived Human iPS Cells Generate Optic Vesicle-Like Structures with the Capacity to Form Retinal Laminae and Develop Synapses," *Investigative Ophthalmology & Visual Science*, 53(4): 2007-2019 (2012).

* cited by examiner

*Primary Examiner* — Taeyoon Kim
(74) *Attorney, Agent, or Firm* — Leydig, Voit & Mayer, Ltd.

(57) ABSTRACT

The invention provides a method for producing a cell aggregate containing a ciliary marginal zone-like structure by culturing a cell aggregate containing a retinal tissue in which Chx10 positive cells are present in a proportion of 20% or more of the tissue in a serum-free medium or serum-containing medium, each containing a substance acting on the Wnt signal pathway for only a period before the appearance of a RPE65 gene expressing cell, followed by culturing the "cell aggregate in which a RPE65 gene expressing cell does not appear" thus obtained in a serum-free medium or serum-containing medium, each not containing a substance acting on the Wnt signal pathway and so on.

15 Claims, 6 Drawing Sheets

METHOD FOR PRODUCING CILIARY MARGINAL ZONE-LIKE STRUCTURE

CROSS-REFERENCE TO RELATED APPLICATOINS

This patent application is the U.S. national phase of International Patent Application No. PCT/JP2013/065878, filed Jun. 7, 2013, which claims the benefit of Japanese Patent Application No. 2012-130521, filed on Jun. 8, 2012, which are incorporated by reference in their entireties herein.

TECHNICAL FIELD

The present invention relates to a method for producing a ciliary marginal zone-like structure, and so on.

BACKGROUND ART

The ciliary marginal zone of the in vivo retina is known to perform important functions for the structural formation and maintenance of retinal tissues (see, for example, non-patent document 1) and, for example, Rdh10 gene (non-patent document 2) and Otx1 gene (non-patent document 1) are known as gene markers of the ciliary marginal zone. However, there is no known method for producing such ciliary marginal zone-like structure from pluripotent stem cells with high efficiency.

DOCUMENT LIST

Non-Patent Documents non-patent document 1: W. Zac Stephens, Megan Senecal, Minhtu Nguyen, and Tatjana Piotrowski (2010) Loss of adenomatous polyposis coli (apc) Results in an Expanded Ciliary Marginal Zone in the Zebrafish Eye. DEVELOPMENTAL DYNAMICS Volume: 239, Pages: 2066-2077 non-patent document 2: Fumi Kubo and Shinichi Nakagawa (2009) Hairy1 acts as a node downstream of Wnt signaling to maintain retinal stem cell-like progenitor cells in the chick ciliary marginal zone. Development Volume: 136, Pages: 1823-1833

SUMMARY OF THE INVENTION

Problems to be Solved by the Invention

There has been a desire to develop a method for producing a ciliary marginal zone-like structure with high efficiency.

Means of Solving the Problems

The present inventors have conducted intensive studies in view of such situation and arrived at the present invention. Specifically, the present invention provides:

1. a method for producing a cell aggregate comprising a ciliary marginal zone-like structure, comprising a step of culturing a cell aggregate comprising a retinal tissue in which Chx10 positive cells are present in a proportion of 20% or more of the tissue in a serum-free medium or serum-containing medium each containing a substance acting on the Wnt signal pathway for only a period before the appearance of a RPE65 gene expressing cell, followed by culturing the "cell aggregate in which a RPE65 gene expressing cell does not appear" thus obtained in a serum-free medium or serum-containing medium each not containing a substance acting on the Wnt signal pathway (hereinafter, sometimes referred to as the production method of the present invention);

2. the production method of the above-mentioned item 1, wherein the period before the appearance of a RPE65 gene expressing cell is a period during which Chx10 positive cells are present in the retinal tissue in a proportion of within 50% to 1% of the tissue, and the cell aggregate in which a RPE65 gene expressing cell does not appear is a cell aggregate in which Chx10 positive cells are present in the retinal tissue in a proportion of within 50% to 1% of the tissue;

3. the production method of the above-mentioned item 2, wherein the "cell aggregate in which a RPE65 gene expressing cell does not appear" thus obtained is cultured in a serum-free medium or serum-containing medium each not containing a substance acting on the Wnt signal pathway until the proportion of Chx10 positive cells present in the retinal tissue reaches 50% or more of the tissue;

4. the production method of any of the above-mentioned items 1 to 3, wherein the retinal tissue is derived from a human pluripotent stem cell;

5. use of a cell aggregate comprising a ciliary marginal zone-like structure produced by the production method of any of the above-mentioned items 1 to 4, as a reagent for evaluating toxicity or drug efficacy;

6. use of a cell aggregate comprising a ciliary marginal zone-like structure produced by the production method of any of the above-mentioned items 1 to 4, as a biological material for transplantation;

and so on.

Effect of the Invention

According to the production method of the present invention, a ciliary marginal zone-like structure can be produced with high efficiency. In a cell aggregate comprising a ciliary marginal zone-like structure produced by the production method of the present invention, the ciliary marginal zone-like structure functions as a progress zone, and there can be formed with high frequency a continuous neural retina having a layer structure adjacent to the ciliary marginal zone-like structure.

BRIEF DESCRIPTION OF THE DRAWINGS

FIG. 11 shows a staining image of a cryosection of a region containing a ciliary marginal zone-like structure contained in a cell aggregate prepared as shown below. A cell aggregate on day 18 after the start of suspension culture was suspension cultured for 3 days in a serum-free medium containing a substance acting on the Wnt signal pathway and suspension cultured for 46 days in a serum-containing medium not containing a substance acting on the Wnt signal pathway, then cultured for 1 day in the presence of BrdU, then cultured for 13 days in the absence of BrdU, cultured for 1 day in the presence of EdU (Invitrogen), and further cultured for 13 days in the absence of EdU. Cryosections of the obtained cell aggregate were prepared and subjected to fluorescence immunostaining with an anti-Ki67 antibody (left Figure) or an anti-BrdU antibody (right Figure) or an anti-Rdh10 antibody (lower Figure), or color development reaction with EdU (middle Figure).

FIG. 12A is an example of a cell aggregate under said conditions, and shows a phase contrast image of a cell aggregate without a ciliary marginal zone-like structure (CMZ) (A, left row, upper panel), a GFP fluorescence image of Crx gene expressing cells in a cell aggregate without a ciliary marginal zone-like structure (A, left row, lower panel), a phase contrast image of a cell aggregate containing a ciliary marginal zone-like structure (A, right row, upper panel), and a GFP fluorescence image of a Crx gene expressing cell in a cell aggregate containing a ciliary marginal zone-like structure (A, right row, lower panel).

FIG. 12B is a graph relating to cell aggregates without a ciliary marginal zone-like structure (CMZ−) and cell aggregates with a ciliary marginal zone-like structure (CMZ+), which shows the measurement results of the proportion of cell aggregates containing continuous, stratified neural retina in not less than 10% of the circumference of the cell aggregate, by using the form of the Crx gene expressing cell as an index.

MODE(S) FOR CARRYING OUT THE INVENTION

Mode(s) for carrying out the present invention is explained in detail below.

In the present invention, examples of the "stem cell" include a cell that maintains the same differentiation capacity even after cell division and can regenerate a tissue when it is injured. Here, the "stem cell" may be an embryonic stem cell (ES cell) or a tissue stem cell (also called tissular stem cell, tissue-specific stem cell or somatic stem cell), or an artificial pluripotent stem cell (iPS cell: induced pluripotent stem cell) but is not limited thereto. As is appreciated from the fact that the stem cell-derived tissue cell can regenerate a tissue, it is known that the stem cell can differentiate into a normal cell close to one in a living body.

Examples of the "pluripotent stem cell" in the present invention include a stem cell that can be cultured in vitro and has an ability to differentiate into any cell (triploblast (ectoderm, mesoderm, endoderm)-derived tissue) constituting a living body except for placenta (pluripotency), including an embryonic stem cell (ES cell). The "pluripotent stem cell" is obtained from fertilized egg, clone embryo, reproductive stem cell, and stem cell in a tissue. It also includes a cell having artificial pluripotency similar to that of embryonic stem cells, after introducing several kinds of genes into a somatic cell (also called artificial pluripotent stem cell). Pluripotent stem cell can be produced by a method known per se. Examples of the production method include the methods described in Cell 131(5) pp. 861-872 (2007), Cell 126(4) pp. 663-676 (2006), etc.

Examples of the "embryonic stem cell (ES cell)" in the present invention include a stem cell having a self replication ability and multipotency (i.e., "pluripotency"), which is a pluripotent stem cell derived from an early embryo. Embryonic stem cell was first established in 1981, and has also been applied to the generation of knockout mouse since 1989. In 1998, a human embryonic stem cell was established, which is also being utilized for regenerative medicine.

Examples of the "artificial pluripotent stem cell" in the present invention include a cell induced to have multipotency by directly reprogramming a differentiated cell such as fibroblast etc. by the expression of several kinds of genes such as Oct3/4, Sox2, Klf4, and Myc, which was established by Yamanaka et al. in mouse cell in 2006 (Takahashi K, Yamanaka S. Cell. 2006, 126(4), p 663-676). In 2007, the artificial pluripotent stem cell was also established in human fibroblast, and has multipotency similar to that of embryonic stem cells (Takahashi K, Tanabe K, Ohnuki M, Narita M, Ichisaka T, Tomoda K, Yamanaka S. Cell. 2007, 131(5), p 861-872.; Yu J, Vodyanik M A, Smuga-Otto K, Antosiewicz-Bourget J, Frane J L, Tian S, Nie J, Jonsdottir G A, Ruotti V, Stewart R, Slukvin II, Thomson J A., Science. 2007, 318(5858), p 1917-1920.; Nakagawa M, Koyanagi M, Tanabe K, Takahashi K, Ichisaka T, Aoi T, Okita K, Mochiduki Y, Takizawa N, Yamanaka S. Nat Biotechnol., 2008, 26(1), p 101-106).

Pluripotent stem cells are available from given organizations, or a commercially available product can be purchased. For example, human embryonic stem cells, KhES-1, KhES-2 and KhES-3, are available from Kyoto University's Institute for Frontier Medical Sciences. EB5 cell, which is a mouse embryonic stem cell, is available from RIKEN, and D3 cell line is available from ATCC, respectively.

Pluripotent stem cell can be maintained by culturing according to a method known per se. For example, human stem cell can be maintained by culturing using Knockout Serum Replacement (KSR). For example, mouse stem cell can be maintained by culturing with addition of fetal bovine serum (FCS) and LIF, and without feeder cell.

Examples of the "tissue" in the present invention include a structure of a cell population, which has a conformation wherein more than one type of cell different in the shape and property are sterically configured in a given pattern.

In the present invention, examples of the "retinal tissue" include a retinal tissue etc. wherein at least two or more types of cells such as photoreceptors, horizontal cells, bipolar cells, amacrin cells, retinal ganglion cells, their precursor cells, retinal progenitor cells thereof and so on, which constitute respective retinal layers in in vivo retina, are sterically arranged in layers. With regard to each cell, which cell constitutes which retinal layer can be confirmed by a known method, for example, presence or absence of the expression of a cell marker or the level thereof, etc.

Examples of the retina cell marker include Rax (progenitor cell of retina), PAX6 (progenitor cell), Chx10 (neural retinal progenitor cell), nestin (expressed in progenitor cell of hypothalamus neuron but not expressed in retinal progenitor cell), Sox1 (expressed in hypothalamus neuroepithelium but not expressed in retina), Crx (precursor cell of photoreceptor), and so on. Examples of the marker of the above-mentioned retinal layer-specific neuron include Chx10 (neural retinal precursor cell or bipolar cell), L7 (bipolar cell), Tuj1 (ganglion cell), Brn3 (ganglion cell), Calretinin (amacrine cell), Calbindin (horizontal cell), Rhodopsin (photoreceptor), Recoverin (photoreceptor), RPE65 (pigment epithelium), Mitf (pigment epithelium) Nrl (rod cell), Rxr-gamma (cone cell) and so on.

The "retinal layer" in the present invention means each layer constituting the retina. Specific examples thereof include retinal pigment epithelial layer, photoreceptor layer, external limiting membrane, outer nuclear layer, outer plexiform layer, inner nuclear layer, inner plexiform layer, ganglion cell layer, nerve fiber layer and inner limiting membrane.

Examples of the "ciliary marginal zone (CMZ)" in the present invention include a tissue present in the boundary region of retinal tissue (specifically, neural retina) and retinal pigment epithelium in the in vivo retina, which is a region including a tissue stem cell of retina (retinal stem cell). Examples of the marker gene of the ciliary marginal zone include Rdh10 gene (positive), Otx1 gene (positive) and so on. It is known that the ciliary marginal zone plays an important role in the supply of retinal progenitor cells and differentiated cells to retinal tissues, maintenance of retinal tissue structure and so on.

Examples of the "progress zone" in the present invention include a population of undifferentiated cells localized in a part of a tissue, and examples thereof include a population of cells having properties to continuously grow in the process of development and regeneration to contribute to the growth of a tissue as a whole and/or properties to contribute to the growth of the surrounding tissues by secreting a growth factor etc. Specific examples of the progress zone include a population of undifferentiated cells at the tip of a limb bud.

Examples of the "aggregate" in the present invention include a mass of the cells dispersed in the medium but gathered to form same. The "aggregate" in the present invention includes an aggregate formed by the cells dispersed at the start of the suspension culture and an aggregate already formed at the start of the suspension culture.

When cells gather to form cell aggregates and the aggregates are subjected to suspension culture, to "form aggregate" means to "rapidly aggregate a given number of dispersed stem cells" to form qualitatively uniform cell aggregates.

Examples of the experimental operation to form an aggregate include a method involving keeping cells in a small space by using a plate with small wells (96 well plate), micropore and so on, a method involving aggregating cells by centrifugation for a short time using a small centrifugation tube, and so on.

The "medium" to be used in the present invention can be prepared from a medium used for culture of animal cell as a basal medium. Examples of the basal medium include media that can be used for culturing animal cells such as BME medium, BGJb medium, CMRL1066 medium, Glasgow MEM medium, Improved MEM Zinc Option medium, IMDM medium, Medium199 medium, Eagle MEM medium, αMEM medium, DMEM medium, ham medium, RPMI1640 medium, Fischer's medium, and mixed medium thereof etc.

Examples of the "serum-free medium" in the present invention include a medium free of unadjusted or unpurified serum. In the present invention, a medium containing purified blood-derived components and animal tissue-derived components (e.g., growth factor) is also included in a serum-free medium unless unadjusted or unpurified serum is contained therein.

To avoid complicated preparation, a serum-free medium (GMEM or DMEM, 0.1 mM 2-mercaptoethanol, 0.1 mM non-essential amino acid Mix, 1 mM sodium pyruvate) added with an appropriate amount (e.g., 1-20%) of commercially available KSR can be preferably mentioned as the serum-free medium.

In addition, the serum-free medium may contain a serum replacement. Examples of the serum replacement include albumin, transferrin, fatty acid, collagen precursor, trace element, 2-mercaptoethanol or 3' thiolglycerol, one appropriately containing equivalents of these etc., and so on. Such serum replacement may be prepared by, for example, the method described in WO98/30679 and so on. In addition, the serum replacement may be a commercially available product. Examples of such commercially available serum replacement include Chemically-defined Lipid concentrated (manufactured by Gibco), Glutamax (manufactured by Gibco) and so on.

The "serum-free medium" to be used for suspension culture may contain fatty acid, lipid, amino acid (e.g., non-essential amino acid), vitamin, growth factor, cytokine, antioxidant, 2-mercaptoethanol, pyruvic acid, buffering agent, inorganic salts and so on.

Examples of the "serum-containing medium" in the present invention include a medium containing unadjusted or unpurified serum. The medium may contain fatty acid, lipid, amino acid (e.g., non-essential amino acid), vitamin, growth factor, cytokine, antioxidant, 2-mercaptoethanol, pyruvic acid, buffering agent, inorganic salts and so on.

Examples of the "suspension culture" in the present invention include culture of cell aggregates in a medium under non-adhesive conditions to a cell culture vessel, and so on.

The cell culture vessel to be used in suspension culture is not particularly limited as long as it enables suspension culture of the cells. Examples of such cell culture vessel include flask, tissue culture flask, dish, petri dish, tissue culture dish, multidish, microplate, microwell plate, micropore, multiplate, multiwell plate, chamber slide, schale, tube, tray, culture bag, roller bottle and so on. A preferable vessel is a cell non-adhesive vessel.

As a cell non-adhesive vessel, one having its surface not artificially treated to improve cell adhesiveness (e.g., coating treatment with extracellular matrix, etc.) and so on may be used.

Examples of the "serum" to be added to the medium in the present invention include mammalian sera such as bovine serum, calf serum, fetal bovine serum, horse serum, colt serum, fetal horse serum, rabbit serum, leveret serum, fetal rabbit serum, and human serum, and so on.

The production method of the present invention characteristically includes a step of culturing a cell aggregate comprising a retinal tissue in which Chx10 positive cells are present in a proportion of 20% or more of the tissue in a serum-free medium or serum-containing medium each containing a substance acting on the Wnt signal pathway for only a period before the appearance of a RPE65 gene expressing cell, followed by culturing the "cell aggregate in which a RPE65 gene expressing cell does not appear" thus obtained in a serum-free medium or serum-containing medium each not containing a substance acting on the Wnt signal pathway. The "cell aggregate comprising a ciliary marginal zone-like structure" produced by the production method of the present invention is useful as a reagent for use for the evaluation of toxicity or drug efficacy of chemical substances and so on, or a material for use for the tests or treatments aiming at cell therapy and so on.

The "cell aggregate comprising a retinal tissue" to be used as a starting material in the production method of the present invention is a cell aggregate in which Chx10 positive cells are present in the retinal tissue in a proportion of 20% or more of the tissue. The aforementioned "proportion of Chx10 positive cells" is, for example, preferably not less than 40%, more preferably not less than 60%, particularly preferably not less than 80%.

The "cell aggregate comprising a retinal tissue" to be used as a starting material in the production method of the present invention can be prepared, for example, from a pluripotent stem cell (preferably human pluripotent stem cell). Specifically, for example, it can be prepared by a method including the following steps (1) to (3).

(1) a first step of subjecting pluripotent stem cells to suspension culture in a serum-free medium containing a substance inhibiting the Wnt signal pathway to form an aggregate of pluripotent stem cells,
(2) a second step of subjecting the aggregate formed in the first step to suspension culture in a serum-free medium containing a basement membrane preparation, and
(3) a third step of subjecting the aggregate cultured in the second step to suspension culture in a serum-containing medium.

A substance inhibiting the Wnt signal pathway to be used in the first step is not particularly limited as long as it can suppress signal transduction mediated by Wnt. Examples of the substance inhibiting the Wnt signal pathway include Dkk1, Cerberus protein, Wnt receptor inhibitor, soluble-type Wnt receptor, Wnt antibody, casein kinase inhibitor, dominant negative Wnt protein, CKI-7 (N-(2-aminoethyl)-5-chloro-isoquinoline-8-sulfonamide), D4476 (4-{4-(2,3-dihydrobenzo[1,4]dioxin-6-yl)-5-pyridin-2-yl-1H-imidazol-2-yl}benzamide), IWR-1-endo (IWR1e), IWP-2 and so on. The concentration of the substance inhibiting the Wnt signal pathway only needs to be a concentration at which aggregates of pluripotent stem cells are formed. For example, a common substance inhibiting the Wnt signal pathway such as IWR1e is added at a concentration of about 0.1 μM to 100 μM, preferably about 1 μM to 10 μM, more preferably about 3 μM.

A substance inhibiting the Wnt signal pathway may be added to serum-free medium before the start of the suspension culture, or added to a serum-free medium within several days from the start of the suspension culture (e.g., within 5 days). Preferably, a substance inhibiting the Wnt signal pathway is added to a serum-free medium within 5 days, more preferably within 3 days, from the start of the suspension culture, most preferably simultaneously with the start of the suspension culture. In addition, suspension culture is performed up to day 18, more preferably day 12, from the start of the suspension culture with the addition of a substance inhibiting the Wnt signal pathway.

The culture conditions such as culture temperature, and $CO_2$ concentration in the first step can be appropriately determined. While the culture temperature is not particularly limited, it is, for example, about 30 to 40° C., preferably about 37° C. The $CO_2$ concentration is, for example, about 1 to 10%, preferably around 5%.

The concentration of the pluripotent stem cells in the first step can be determined as appropriate by those of ordinary skill in the art to form aggregates of pluripotent stem cells more uniformly and efficiently. The concentration of the pluripotent stem cells when forming aggregates is not particularly limited as long as it permits formation of uniform aggregates of stem cells. For example, when human ES cells are subjected to suspension culture using a 96 well microwell plate, a liquid prepared to about $1\times10^3$ to about $5\times10^4$ cells, preferably about $3\times10^3$ to about $3\times10^4$ cells, more preferably about $5\times10^3$ to about $2\times10^4$ cells, most preferably around $9\times10^3$ cells, per well is added, and the plate is left standing to form aggregates.

The time of suspension culture necessary for forming aggregates can be determined as appropriate according to the pluripotent stem cell to be used, as long as the cells can be aggregated rapidly. To form uniform aggregates, it is desirably as short as possible. For example, in the case of human ES cells, aggregates are desirably formed preferably within 24 hr, more preferably within 12 hr. The time for aggregate formation can be appropriately adjusted by those of ordinary skill in the art by controlling the tools for aggregating the cells, centrifugation conditions and so on.

Those of ordinary skill in the art can determine whether aggregates of pluripotent stem cells have been formed, based on the size and cell number of aggregates, macroscopic morphology, microscopic morphology by tissue staining analysis and uniformity thereof, expression of differentiation and undifferentiation markers and uniformity thereof, control of expression of differentiation marker and synchronism thereof, reproducibility of differentiation efficiency between aggregates, and so on.

The basement membrane preparation to be used in the second step refers to one containing basement membrane-constituting components having a function to control cell morphology, differentiation, growth, motility, expression of function and so on which are similar to those of epithelial cell, when intended cells capable of forming a basement membrane are plated thereon and cultured. Here, the "basement membrane constituting component" refers to an extracellular matrix molecule in the morphology of a thin membrane present between epithelial cell layer and interstitial cell layer and so on in animal tissues. A basement membrane preparation can be produced by, for example, removing cells capable of forming a basement membrane, which adhere onto a support via a basement membrane, with a solution capable of dissolving the lipid of the cells, an alkali solution and so on. Examples of preferable basement membrane preparation include products commercially available as basement membrane components (e.g., Matrigel (hereinafter, sometimes referred to as Matrigel)), and extracellular matrix molecules known as basement membrane components (e.g., laminin, type IV collagen, heparan sulfate proteoglycan, entactin and so on).

Matrigel is a product prepared from a basement membrane derived from Engelbreth Holm Swarn (EHS) mouse sarcoma. The main component of Matrigel is type IV collagen, laminin, heparan sulfate proteoglycan, and entactin. In addition to these, TGF-β, fibroblast growth factor (FGF), tissue plasminogen activator, and a growth factor naturally produced by EHS tumor are contained. The "growth factor reduced (GFR) product" of Matrigel has a lower growth factor concentration than common Matrigel. In the present invention, GFR product is preferably used.

While the concentration of the basement membrane preparation to be added to a serum-free medium for the suspension culture in the second step is not particularly limited as long as the epithelial structure of the neural tissue (e.g., retinal tissue) is stably maintained, for example, it is preferably 1/20 to 1/200 volume, more preferably around 1/100 volume, of the culture medium when Martigel is used. While basement membrane preparation may already have been added to the medium when the culture of stem cell is started, it is preferably added to the serum-free medium within 5 days, more preferably within 2 days, from the start of the suspension culture.

As the serum-free medium to be used in the second step, the serum-free medium used in the first step may be directly used, or may be replaced with a fresh serum-free medium.

When the serum-free medium used in the first step is directly used for this step, the "basement membrane preparation" can be added to the medium.

The culture conditions such as culture temperature, and $CO_2$ concentration in the second step can be appropriately determined. While the culture temperature is not particularly limited, it is, for example, about 30 to 40° C., preferably around 37° C. The $CO_2$ concentration is, for example, about 1 to 10%, preferably around 5%.

As the serum-containing medium to be used in the third step, may be used the serum-free medium used in the culture of the second step to which a serum is directly added, or one replaced with a fresh serum-containing medium.

The serum is added on or after day 7, more preferably on or after day 9, most preferably on day 12, from the start of the suspension culture. The concentration of the serum to be added is about 1 to 30%, preferably about 3 to 20%, more preferably around 10%.

In the third step, the production efficiency of retinal tissue can be increased by adding a substance acting on the Shh signal pathway in addition to the serum.

The substance acting on the Shh signal pathway is not particularly limited as long as it can enhance signal transduction mediated by Shh. Examples of the substance acting on the Shh signal pathway include proteins belonging to the Hedgehog family (e.g., Shh), Shh receptor, Shh receptor agonist, Purmorphamine, SAG and so on.

The concentration of the substance acting on the Shh signal pathway used in this step is, for example, in the case of common substance acting on the Shh signal pathway such as SAG, about 0.1 nM to 10 μM, preferably about 10 nM to 1 μM, more preferably around 100 nM.

The retinal tissue thus produced is present to cover the surface of the aggregate. Whether a retinal tissue is produced can be confirmed by immunostaining method etc.

For example, the aggregate cultured in the third step is subjected to suspension culture in a serum-containing medium. Examples of the cell culture vessel to be used for suspension culture include those mentioned above. The culture conditions such as culture temperature, $CO_2$ concentration, and $O_2$ concentration of the suspension culture can be appropriately determined. While the culture temperature is not particularly limited, it is, for example, about 30 to 40° C., preferably about 37° C. The $CO_2$ concentration is, for example, about 1 to 10%, preferably about 5%. The $O_2$ concentration is, for example, 20 to 70%, preferably 20 to 60%, more preferably 30 to 50%. While the culture period is not particularly limited, it is generally not less than 48 hr, preferably not less than 7 days.

After completion of the suspension culture, the aggregates are fixed with a fixative such as para-formaldehyde solution and so on, and a cryosection is prepared. The obtained cryosection is immunostained, and formation of a layer structure of retinal tissue is confirmed. Since respective layers of a retinal tissue are composed of different retinal progenitor cells (photoreceptor, horizontal cell, bipolar cell, amacrine cell, retinal ganglion cell), formation of a layer structure can be confirmed by immunostaining using antibodies against the aforementioned markers expressed in these cells.

The "proportion of Chx10 positive cells" in a retinal tissue contained in a cell aggregate produced as mentioned above can be examined by, for example, the following method.

(1) First, a cryosection of "a cell aggregate comprising a retinal tissue" is prepared.
(2) Then, immunostaining of Rax protein or, when a gene recombinant cell obtained by altering a Rax gene expressing cell to express a fluorescence protein such as GFP is used, the expression of the aforementioned fluorescence protein, is observed using a fluorescence microscope and so on, whereby a retinal tissue region expressing Rax gene is specified.
(3) Using the same section as the cryosection wherein the retinal tissue region expressing Rax gene has been specified or an adjacent section as a sample, the nucleus is stained with a nuclear staining reagent such as Dapi. Then, the number of stained nuclei in the above-specified retinal tissue region expressing Rax gene is counted, whereby the number of the cells in the retinal tissue region is measured.
(4) Using the same section as the cryosection wherein the retinal tissue region expressing Rax gene has been specified or an adjacent section as a sample, Chx10 protein is immunostained. The number of Chx10 positive cells in the above-specified retinal tissue region is counted.
(5) Based on each number of nuclei measured in the above-mentioned (3) and (4), the number of nuclei in Chx10 positive cells is divided by the number of nuclei in the Chx10 positive cells in the above-specified retinal tissue region, whereby the "proportion of Chx10 positive cells" is calculated.

In the production method of the present invention, firstly, a cell aggregate comprising a retinal tissue in which Chx10 positive cells are present in a proportion of 20% or more of the tissue is cultured in a serum-free medium or serum-containing medium each containing a substance acting on the Wnt signal pathway for only a period before the appearance of a RPE65 gene expressing cell.

As a preferable culture here, suspension culture can be mentioned. As a preferable medium, a serum-free medium can be mentioned.

The culture conditions such as culture temperature, $CO_2$ concentration can be appropriately set. The culture temperature is, for example, in the range of about 30° C. to about 40° C., preferably, for example, around 37° C. The $CO_2$ concentration is, for example, in the range of about 1% to about 10%, preferably, for example, around 5%.

The substance acting on the Wnt signal pathway to be contained in a serum-free medium or serum-containing medium when the above-mentioned "cell aggregate comprising a retinal tissue" is cultured in the medium is not particularly limited as long as it can enhance signal transduction mediated by Wnt. Specific examples of the substance acting on the Wnt signal pathway include protein belonging to Wnt family, Wnt receptor, Wnt receptor agonist, GSK3β inhibitor (e.g., 6-Bromoindirubin-3'-oxime (BIO), CHIR99021, Kenpaullone) and so on.

The concentration of the substance acting on the Wnt signal pathway to be contained in a serum-free medium or serum-containing medium in the case of a common substance acting on the Wnt signal pathway such as CHIR99021 is, for example, in the range of about 0.1 μM to 100 μM, preferably, for example, in the range of about 1 μM to 30 μM, more preferably, for example, around 3 μM.

"Culturing for only a period before the appearance of a RPE65 gene expressing cell" in the production method of the present invention means culturing in the whole or a part of the period before the appearance of a RPE65 gene expressing cell. That is, culturing in the whole or a part of the period (any period) during which the "cell aggregate comprising a retinal tissue" in the culture system is constituted by cells that do not substantially express RPE65 gene suffices. By employing such culturing, a cell aggregate in which a RPE65 gene expressing cell does not appear can be obtained.

To determine such particular period, the "cell aggregate comprising a retinal tissue" is used as a sample, and the presence or absence of expression of RPE65 gene contained in the sample only needs to be measured by a general genetic engineering method. Specifically, for example, as described in the below-mentioned Examples, the presence or absence of expression of RPE65 gene or the level thereof can be examined by subjecting a cryosection of the aforementioned "cell aggregate comprising a retinal tissue" to an immunostaining method using an antibody against RPE65 protein.

A preferable "period before the appearance of a RPE65 gene expressing cell" is, for example, a period during which Chx10 positive cells are present in the retinal tissue in a proportion of within 50% to 1% of the tissue. In this case, the obtained "cell aggregate in which a RPE65 gene expressing cell does not appear" is a cell aggregate in which Chx10 positive cells are present in the retinal tissue in a proportion of within 50% to 1% of the tissue.

While the number of days of the "period before the appearance of a RPE65 gene expressing cell" varies depending on the kind of the substance acting on the Wnt signal pathway, the kind of the serum-free medium or serum-containing medium, other culture conditions and so on, it is, for example, within 5 days. The aforementioned period is preferably, for example, within 4 days, more preferably, for example, 2 days to 3 days.

Then the "cell aggregate in which a RPE65 gene expressing cell does not appear" obtained by culturing as mentioned above is cultured in a serum-free medium or serum-containing medium not containing a substance acting on the Wnt signal pathway.

A preferable culture here is, for example, suspension culture.

Examples of a preferable culture time include a time for culturing until the proportion of the Chx10 positive cells present in the retinal tissue reaches 50% or more of the tissue.

The culture conditions such as culture temperature, $CO_2$ concentration can be appropriately set. The culture temperature is, for example, in the range of about 30° C. to about 40° C., preferably, for example, around 37° C. In addition, the $CO_2$ concentration is, for example, in the range of about 1% to about 10%, preferably, for example, around 5%.

While the number of the above-mentioned culture days until "a cell aggregate comprising a ciliary marginal zone-like structure" is obtained varies depending on the kind of the serum-free medium or serum-containing medium, other culture conditions and so on, it is, for example, within 100 days. The aforementioned number of culture days is preferably, for example, 20 days to 70 days, more preferably, for example, 30 days to 60 days.

In the "cell aggregate comprising a ciliary marginal zone-like structure" thus produced, retinal pigment epithelium and retinal tissue (specifically, neural retina) are present adjacent to the ciliary marginal zone-like structure in the same cell aggregate. The structure can be easily confirmed by microscopic observation and so on.

A highly pure retinal tissue (specifically, neural retina) can be prepared by physically cutting out a retinal tissue (specifically, neural retina) from the aforementioned "cell aggregate comprising a ciliary marginal zone-like structure" with tweezers etc. A highly pure retinal tissue (specifically, neural retina) can be further continuously cultured (specifically, long-term culture for, for example, 60 days or longer) while maintaining the good tissue structure it has. The culture conditions such as culture temperature, $CO_2$ concentration, $O_2$ concentration can be those generally used for tissue culture. In this case, culture may be performed in the presence of a serum, a known growth factor, an additive and a chemical substance that promote the growth, and so on. Examples of the known growth factor include EGF, FGF and so on. Examples of the additive that promotes the growth include N2 supplement (Invitrogen), B27 supplement (Invitrogen) and so on.

The present invention also includes use of a cell aggregate comprising a ciliary marginal zone-like structure produced by the production method of the present invention as a reagent for the evaluation of the toxicity or drug efficacy, use of a cell aggregate comprising a ciliary marginal zone-like structure produced by the production method of the present invention as a biological material for transplantation and so on.

<Use of Cell Aggregate Comprising Ciliary Marginal Zone-Like Structure as Reagent for Evaluating Toxicity or Drug Efficacy>

The cell aggregate comprising a ciliary marginal zone-like structure produced by the production method of the present invention can be used for screening for a therapeutic drug for a disease caused by a disorder of retinal cell, a material for the study of diseases or a drug discovery material. It is also utilizable for the evaluation of the toxicity or drug efficacy of a chemical substance and so on, as well as study of toxicity such as phototoxicity, neurotoxicity and so on, toxicity test and so on.

<Use of Cell Aggregate Comprising Ciliary Marginal Zone-Like Structure as Biological Material for Transplantation>

The cell aggregate comprising a ciliary marginal zone-like structure produced by the production method of the present invention can be used as a biological material for transplantation used for supplementing a disordered tissue itself in a cell damage state (e.g., used for transplantation operation) and so on.

EXAMPLES

The present invention is explained in more detail in the following by referring to Examples, which are not to be construed as limitative.

Example 1

Production Example of Cell Aggregate Containing Retinal Tissue Using Human ES Cell—1

RAX::GFP knock-in human ES cells (derived from KhES-1; Nakano, T. et al. Cell Stem Cell 2012, 10(6), 771-785) were cultured according to the methods described in "Ueno, M. et al PNAS 2006, 103(25), 9554-9559" and "Watanabe, K. et al. Nat Biotech 2007, 25, 681-686". As the medium, DMEM/F12 medium (Invitrogen) added with 20% KSR (Knockout Serum Replacement; Invitrogen), 0.1 mM 2-mercaptoethanol, 1 mM pyruvic acid and 5 to 10 ng/ml bFGF was used. The aforementioned cultured ES cells were singly dispersed in 0.25% trypsin-EDTA (Invitrogen), and the singly dispersed ES cells were floated in a 100 µl serum-free medium to $9\times10^3$ cells per well of a non-cell adhesive 96-well culture plate (SUMILON spheroid plate, SUMITOMO BAKELITE CO., LTD.), and suspension-cultured at 37° C., 5% $CO_2$. The serum-free medium used then was a serum-free medium obtained by adding 20% KSR, 0.1 mM 2-mercaptoethanol, 1 mM pyruvic acid, 20 µM Y27632 and Wnt signal pathway inhibitory substance (3 µM IWR1e) to G-MEM medium. During the suspension culture, GFR Matrigel (Invitrogen) in an amount of 1/100 per volume was added from day 2 from the start of the suspension culture. A fetal bovine serum in an amount of 1/10 per volume and a substance acting on the Shh signal pathway (100 nM SAG) were added on day 12 from the start of the suspension culture, and the suspension culture was performed for total 18 days.

Figure 1:
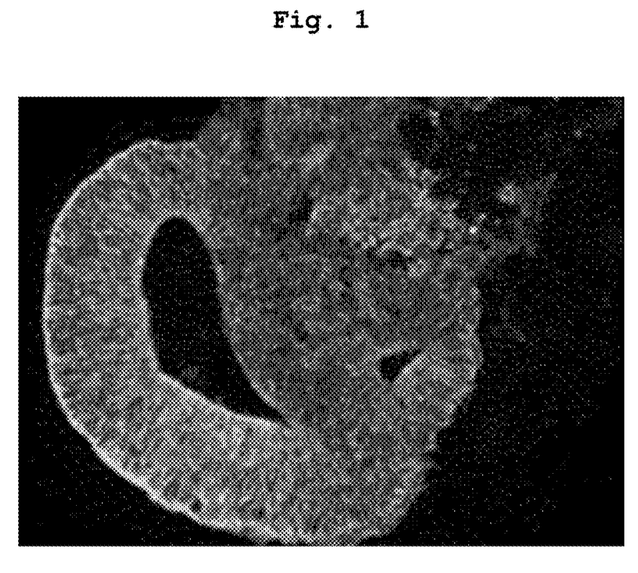
FIG. 1 is a view that shows a GFP fluorescence image of Rax gene expressing cells in a cryosection of cell aggregate before suspension culture in a serum-free medium containing a substance acting on the Wnt signal pathway.
Figure 2:
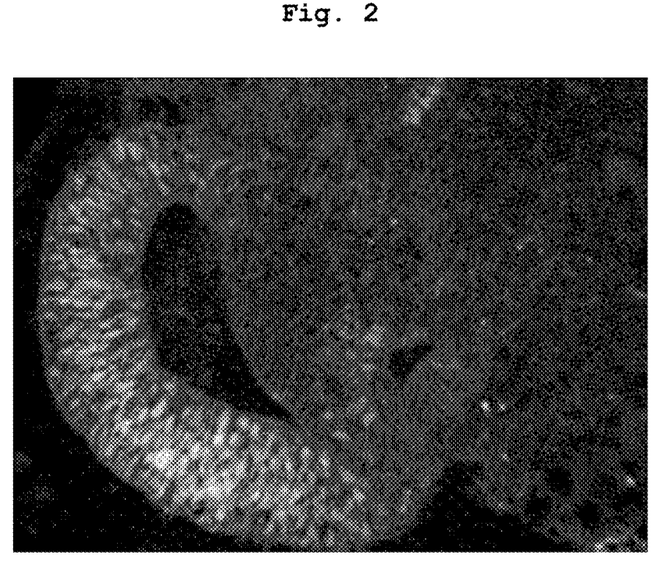
FIG. 2 is a view that shows a fluorescence immunostaining image, using an anti-Chx10 antibody, of a cryosection of cell aggregate before suspension culture in a serum-free medium containing a substance acting on the Wnt signal pathway. Comparison of FIG. 1 (showing presence of whole retinal tissues) and FIG. 2 (showing presence of Chx10 positive cells) confirms presence of Chx10 positive cells in about 40% of the whole before addition of a substance acting on the Wnt signal pathway.

The thus-produced cell aggregate was fixed with 4% para-formaldehyde to produce a cryosection. The prepared cryosection was subjected to fluorescence microscope observation of a GFP fluorescence image (FIGS. 1) and immunostaining with Chx10 which is one of neural retinal progenitor cell markers (FIG. 2). In the retinal tissue contained in the cell aggregate produced as mentioned above, Chx10 positive cells were found in about 40% of the tissue (see FIG. 2).

Example 2

Production Example of Cell Aggregate Containing Retinal Tissue Using Human ES Cell—2

By a method similar to that in Example 1, suspension culture was performed for a longer time. As a result, on day 25 from the start of the suspension culture, a cell aggregate containing a retinal tissue in which Chx10 positive cells were found in about 80% or about 90% of the tissue was also obtained.

Example 3

Culture of Cell Aggregate Containing Retinal Tissue in Serum-Free Medium Containing Substance Acting on Wnt Signal Pathway A cell aggregate containing a retinal tissue on day 18 from the start of the suspension culture, which was produced by the method described in Example 1, was suspension-cultured in a serum-free medium containing a substance acting on the Wnt signal pathway (3 µM CHIR99021) for 3 days.

Figure 3:
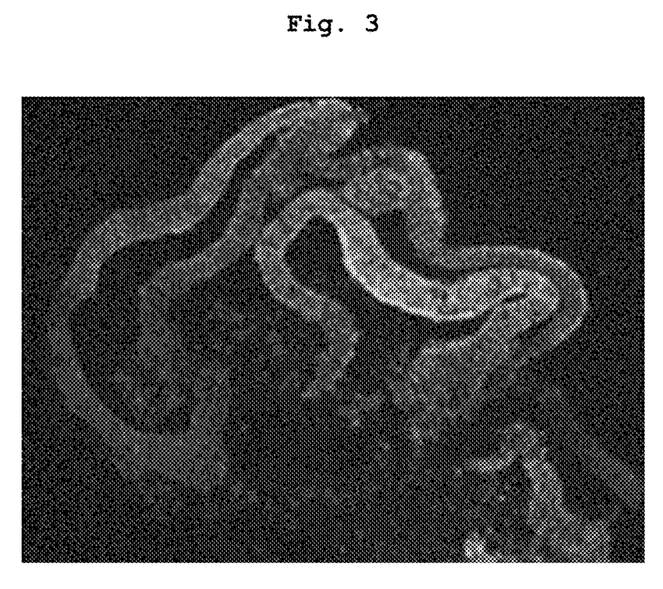
FIG. 3 is a view that shows a GFP fluorescence image of Rax gene expressing cells in a cryosection of cell aggregate on day 3 after suspension culture in a serum-free medium containing a substance acting on the Wnt signal pathway.
Figure 4:
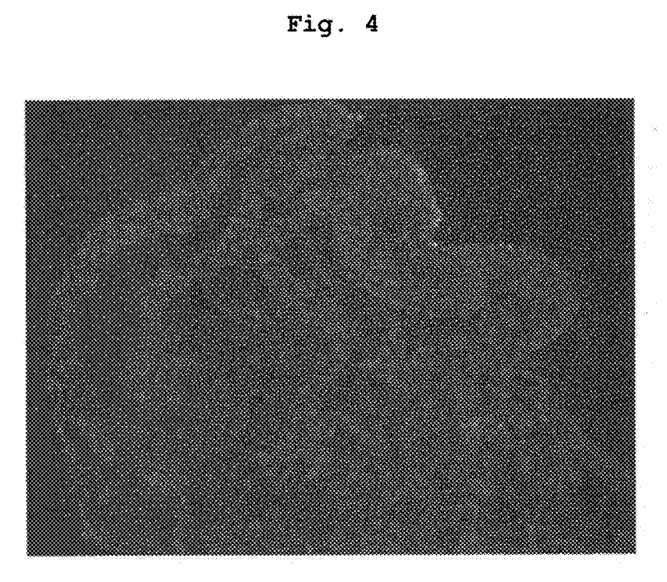
FIG. 4 is a view that shows a fluorescence immunostaining image, using an anti-Chx10 antibody, of a cryosection of cell aggregate on day 3 after suspension culture in a serum-free medium containing a substance acting on the Wnt signal pathway. Comparison of FIG. 3 (showing presence of whole retinal tissues) and FIG. 4 (showing presence of Chx10 positive cells) reveals presence of Chx10 positive cells only in about 3% of the whole in 3 days after addition of a substance acting on the Wnt signal pathway to the medium, whereby a clear decrease can be confirmed.

The obtained cell aggregate was fixed with 4% para-formaldehyde to prepare a cryosection. The prepared cryosection was subjected to fluorescence microscopic observation of a GFP fluorescence image (FIG. 3) and immunostaining with Chx10 which is one of the neural retinal progenitor cell markers (FIG. 4). In the retinal tissue contained in the aforementioned cell aggregate, which had been suspension-cultured in a serum-free medium containing a substance acting on the Wnt signal pathway for 3 days, Chx10 positive cells were found in only about 3% of the tissue and a clear decrease in the proportion of the Chx10 positive cells was observed (see FIG. 4). At that time, a RPE65 gene expressing cell did not appear in the aforementioned cell aggregate.

Example 4

Suspension Culture of "Cell Aggregate in Which a RPE65 Gene Expressing Cell Does not Appear" in Serum-Containing Medium not Containing a Substance Acting on Wnt Signal Pathway—1

The cell aggregate (the proportion of Chx10 positive cells: about 3%) on day 21 from the start of the suspension culture (total days of the above-mentioned "day 18" and "day 3"), which was produced by the methods described in Example 1 and Example 3, was further suspension-cultured in a serum-containing medium (containing DMEM/F12, 10% fetal bovine serum, N2 supplement, 0.5 µM retinoic acid etc.) not containing a substance acting on the Wnt signal pathway under 40% $O_2$ condition for 39 days.

Figure 5:
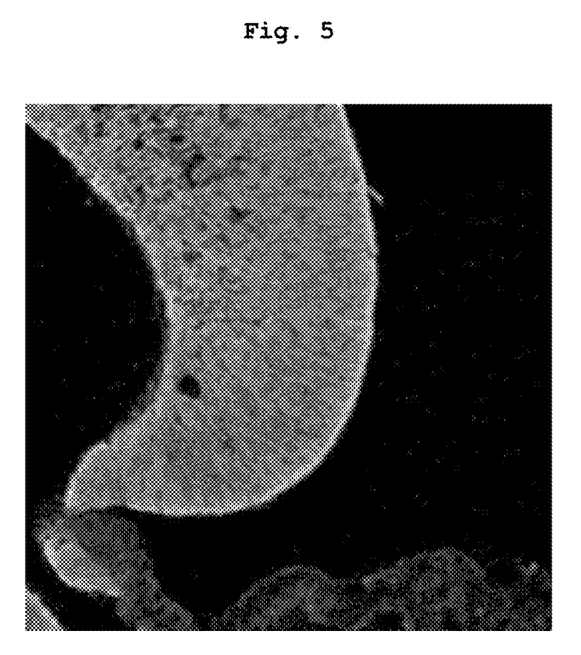
FIG. 5 is a view that shows a GFP fluorescence image of Rax gene expressing cells in a cryosection of cell aggregate after suspension culture for 3 days in a serum-free medium containing a substance acting on the Wnt signal pathway followed by suspension culture for 39 days in a serum-containing medium not containing a substance acting on the Wnt signal pathway.
Figure 6:
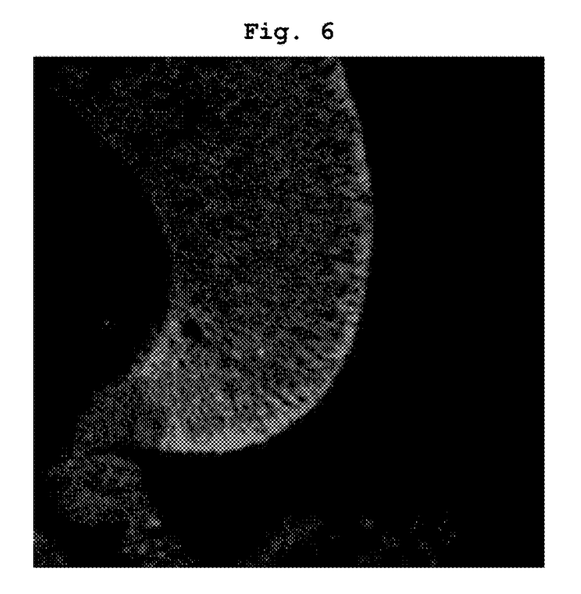
FIG. 6 is a view that shows a fluorescence immunostaining image, using an anti-Rdh10 antibody, of a cryosection of cell aggregate after suspension culture for 3 days in a serum-free medium containing a substance acting on the Wnt signal pathway followed by suspension culture for 39 days in a serum-containing medium not containing a substance acting on the Wnt signal pathway. Comparison of FIG. 5 (showing presence of whole retinal tissues) and FIG. 6 (showing presence of Rdh10 positive cells) confirms presence of Rdh10 positive cells resulting from culturing for 3 days with the addition of a substance acting on the Wnt signal pathway followed by culturing in a serum-containing medium not containing of a substance acting on the Wnt signal pathway.

The obtained cell aggregate was fixed with 4% paraformaldehyde to prepare a cryosection. The prepared cryosection was subjected to fluorescence microscopic observation of a GFP fluorescence image (FIG. 5) and immunostaining with Rdh10 which is one of the ciliary marginal zone markers (FIG. 6). In the manner mentioned above, it could be confirmed in the cell aggregate after suspension culture for 39 days in a serum-containing medium not containing a substance acting on the Wnt signal pathway that Rdh10 positive cells (that is, cells expressing Rdh10 gene which is a marker gene of ciliary marginal zone-like structure) were present as a nearly-uniform group region in the tissue present in the boundary region of retinal tissue (specifically, neural retina) and retinal pigment epithelium, and a cell aggregate containing a ciliary marginal zone-like structure was produced with high efficiency (see FIG. 6).

Example 5

Suspension Culture of "Cell Aggregate in Which a RPE65 Gene Expressing Cell Does not Appear" in Serum-Containing Medium not Containing a Substance Acting on Wnt Signal Pathway—2

The cell aggregate (existence ratio of Chx10 positive cells: about 3%) on day 21 from the start of the suspension culture (total days of the above-mentioned "day 18" and "day 3"), which was produced by the methods described in Example 1 and Example 3, was further suspension-cultured in the same manner as in Example 4 in a serum-containing medium (containing DMEM/F12, 10% fetal bovine serum, N2 supplement, 0.5 µM retinoic acid etc.) not containing a substance acting on the Wnt signal pathway under 40% $O_2$ condition for further 50 days.

Figure 7:
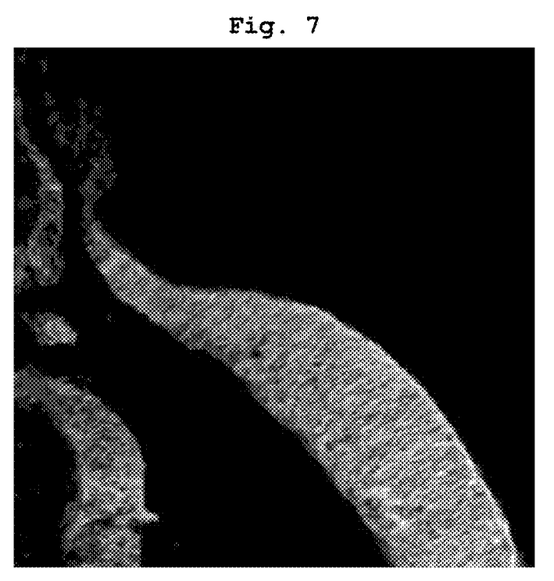
FIG. 7 is a view that shows a GFP fluorescence image of Rax gene expressing cells in a cryosection of cell aggregate after suspension culture for 3 days in a serum-free medium containing a substance acting on the Wnt signal pathway followed by suspension culture for 50 days in a serum-containing medium not containing a substance acting on the Wnt signal pathway.
Figure 8:
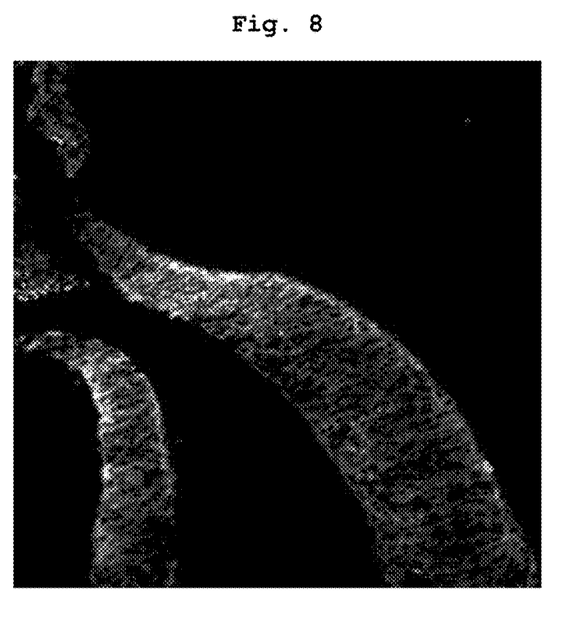
FIG. 8 is a view that shows a fluorescence immunostaining image, using an anti-Rdh10 antibody, of a cryosection of cell aggregate after suspension culture for 3 days in a serum-free medium containing a substance acting on the Wnt signal pathway followed by suspension culture for 50 days in a serum-containing medium not containing a substance acting on the Wnt signal pathway.
Figure 9:
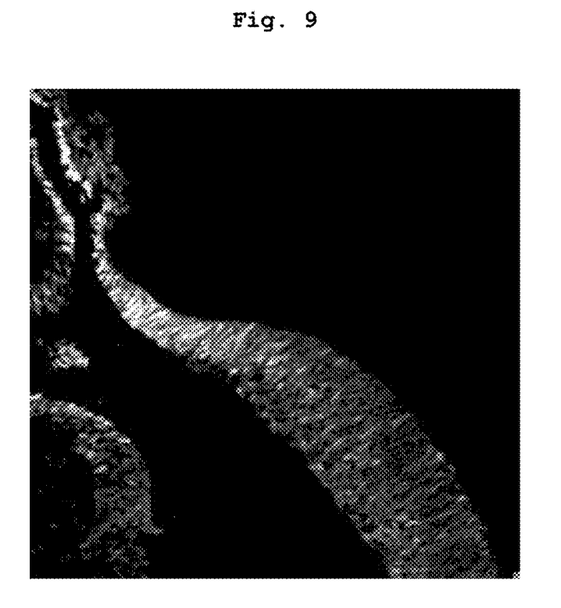
FIG. 9 is a view that shows a fluorescence immunostaining image, using an anti-Otx1 antibody, of a cryosection of cell aggregate after suspension culture for 3 days in a serum-free medium containing a substance acting on the Wnt signal pathway followed by suspension culture for 50 days in a serum-containing medium not containing a substance acting on the Wnt signal pathway. Comparison of FIG. 7 (showing presence of whole retinal tissues), FIG. 8 (showing presence of Rdh10 positive cells) and FIG. 9 (showing presence of Otx1 positive cells) confirms presence of Rdh10 positive cells and Otx1 positive cell resulting from culturing for 3 days with the addition of a substance acting on the Wnt signal pathway followed by culturing in a serum-containing medium not containing of a substance acting on the Wnt signal pathway.

The obtained cell aggregate was fixed with 4% paraformaldehyde to prepare a cryosection. The prepared cryosection was subjected to fluorescence microscopic observation of a GFP fluorescence image (FIG. 7) and immunostaining with Rdh10 (FIG. 8) or Otx1 (FIG. 9) which is one of the ciliary marginal zone markers. In the manner mentioned above, in the cell aggregate after suspension culture for 50 days in a serum-containing medium not containing a substance acting on the Wnt signal pathway, Rdh10 positive cells (that is, cells expressing Rdh10 gene which is a marker gene of ciliary marginal zone-like structure) were present as a nearly-uniform group region in the tissue present in the boundary region of retinal tissue (specifically, neural retina) and retinal pigment epithelium (see FIG. 8), and Otx1 positive cells (that is, cells expressing Otx1 gene which is a marker gene of ciliary marginal zone-like structure) were also similarly present (see FIG. 9). From these results, it could be confirmed that a cell aggregate containing a ciliary marginal zone-like structure was produced with high efficiency by the production method.

Example 6

Analysis of Proliferative Capacity of Cell Aggregate Containing Ciliary Marginal Zone-Like Structure—1

Figure 10:
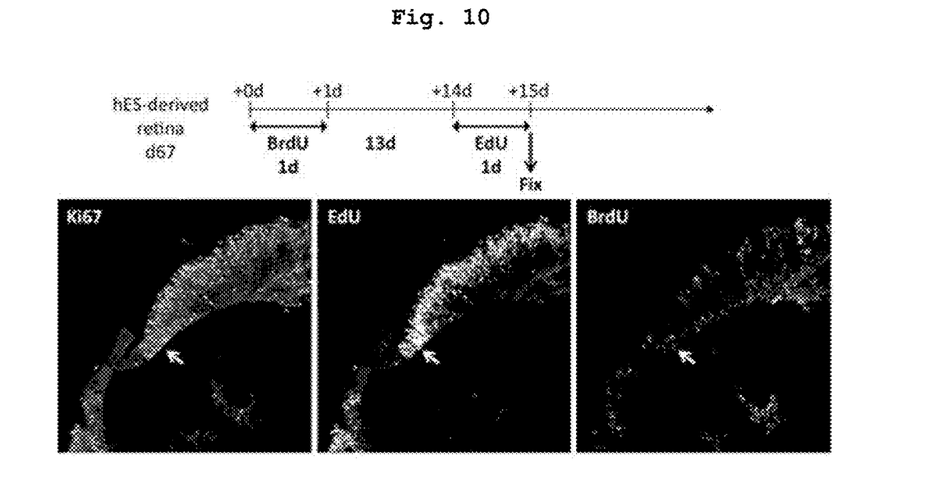
FIG. 10 shows a staining image of a cryosection of a region containing a ciliary marginal zone-like structure contained in a cell aggregate prepared as shown below. A cell aggregate on day 18 after the start of suspension culture was suspension cultured for 3 days in a serum-free medium containing a substance acting on the Wnt signal pathway and suspension cultured for 46 days in a serum-containing medium not containing a substance acting on the Wnt signal pathway, then cultured for 1 day in the presence of BrdU, then cultured for 13 days in the absence of BrdU, and cultured for 1 day in the presence of EdU (Invitrogen). Cryosections of the obtained cell aggregate were prepared and subjected to fluorescence immunostaining with an anti-Ki67 antibody (left Figure) or an anti-BrdU antibody (right Figure), or color development reaction with EdU (middle Figure).

The cell aggregate on day 18 from the start of the suspension culture, which was produced by the method described in Example 1, was suspension-cultured for 3 days in a serum-free medium containing a substance acting on the Wnt signal pathway, and then suspension-cultured in the same manner as in Example 4 and Example 5 for 46 days in a serum-containing medium not containing a substance acting on the Wnt signal pathway. Thereafter, the cell aggregate was cultured in the presence of BrdU for 1 day to label the grown cells, then in the absence of BrdU for 13 days, and in the presence of EdU (Invitrogen) for 1 day. The obtained cell aggregate was fixed with 4% para-formaldehyde to prepare a cryosection. The prepared cryosection was subjected to immunofluorescence staining with anti-Ki67 antibody (FIG. 10, left Figure) or anti-BrdU antibody (FIG. 10, right Figure), or EdU color development reaction (FIG. 10, middle Figure).

As a result, it was found that the ciliary marginal zone-like structure was a Ki67 positive growing cell in the cell aggregate after suspension culture for 46 days in a serum-containing medium not containing a substance acting on the Wnt signal pathway in the manner mentioned above (FIG. 10, left Figure, shown by arrow). It was found that 90% or more of the growing cells can be labeled by EdU uptake for 1 day, since 90% or more of Ki67 positive cells are EdU-positive (FIG. 10, middle Figure, arrow). On the other hand, since Ki67 positive cells in the ciliary marginal zone-like structure showed a weak BrdU signal (FIG. 10, right Figure, arrow), it is assumed that the aforementioned Ki67 positive cells continued to grow for 14 days after BrdU labeling and diluted BrdU uptaken into DNA. From these results, it was found that the ciliary marginal zone-like structure in the cell aggregate cultured as mentioned above is the progress zone.

Example 7

Analysis of Proliferative Capacity of Cell Aggregate Containing Ciliary Marginal Zone-Like Structure—2

Figure 11:
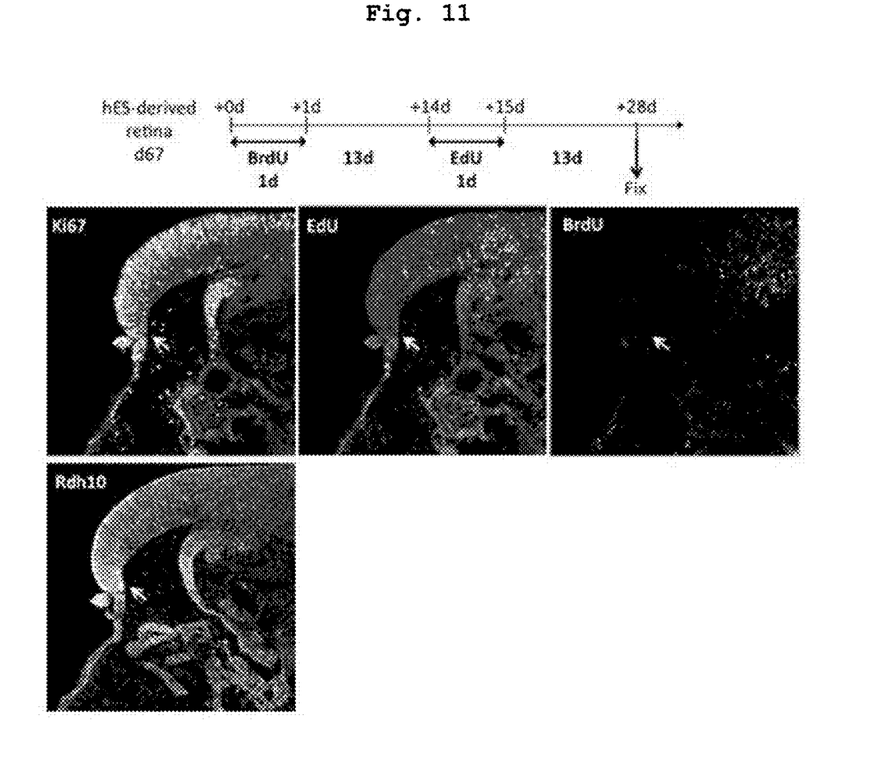

The cell aggregate on day 18 from the start of the suspension culture, which was produced by the method described in Example 1, was suspension-cultured for 3 days in a serum-free medium containing a substance acting on the Wnt signal pathway, and then suspension-cultured in the same manner as in Example 4, Example 5 and Example 6 for 46 days in a serum-containing medium not containing a substance acting on the Wnt signal pathway. Thereafter, the cell aggregate was cultured in the presence of BrdU for 1 day to label the grown cells, then in the absence of BrdU for 13 days, in the presence of EdU (Invitrogen) for 1 day, and further in the absence of EdU for 13 days. A cryosection of the obtained cell aggregate was produced, and subjected to immunofluorescence staining with anti-Ki67 antibody (FIG. 11, left Figure), anti-BrdU antibody (FIG. 11, right Figure) or anti-Rdh10 antibody (FIG. 11, bottom Figure), or EdU color development reaction (FIG. 11, middle Figure).

As a result, it was found that the Rdh10-positive ciliary marginal zone-like structure (FIG. 11, bottom Figure, shown by arrow) was Ki67 positive (FIG. 11, left Figure) in the cell aggregate after suspension culture for 46 days in a serum-containing medium not containing a substance acting on the Wnt signal pathway in the manner mentioned above. The aforementioned Ki67 positive cell in the ciliary marginal zone-like structure was found to show weak EdU (FIG. 11, middle Figure) and BrdU (FIG. 11, right Figure) signals. Therefore, it was assumed that the aforementioned Ki67 positive cell in the aforementioned ciliary marginal zone-like structure continued to grow for 27 days and diluted EdU and BrdU uptaken into DNA. From these results, it was found that the ciliary marginal zone-like structure in the cell aggregate cultured as mentioned above is the progress zone.

Example 8

Figure 12:
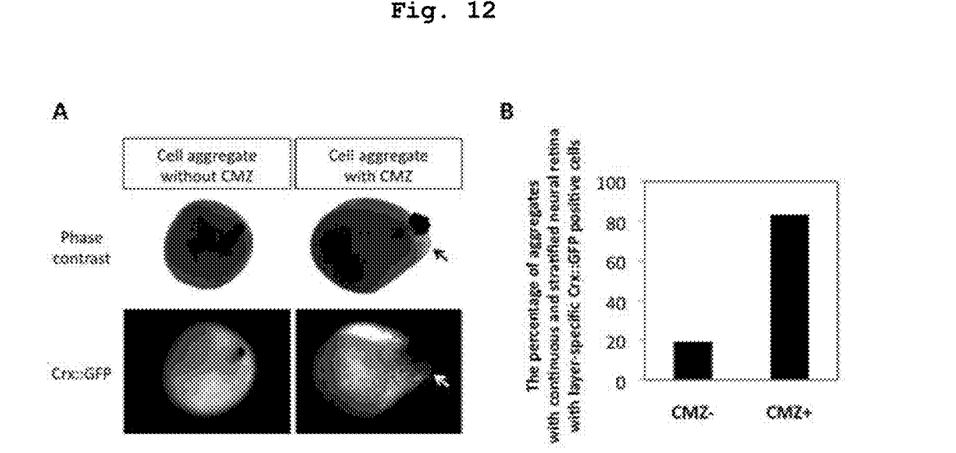
FIG. 12 is a view that shows analysis of a cell aggregate obtained by subjecting a cell aggregate on day 18 after the start of suspension culture to suspension culture for 3 days in a serum-free medium containing a substance acting on the Wnt signal pathway and suspension culture for 75 days in a serum-containing medium not containing a substance acting on the Wnt signal pathway.

Analysis of Morphology of Neural Retina in Cell Aggregate Containing Ciliary Marginal Zone-Like Structure The cell aggregate on day 18 from the start of the suspension culture, which was produced by the method described in Example 1, was suspension-cultured for 3 days in a serum-free medium containing a substance acting on the Wnt signal pathway and, in the same manner as in Example 4, Example 5, Example 6 and Example 7, suspension-cultured for 75 days in a serum-containing medium not containing a substance acting on the Wnt signal pathway, and the obtained cell aggregate was analyzed. As one embodiment of the cell aggregate, a phase contrast image of the cell aggregate without a ciliary marginal zone-like structure (CMZ) (A, left line, the upper panel), a GFP fluorescence image of Crx gene-expressing cells of the cell aggregate without a ciliary marginal zone-like structure (A, left row, lower panel), a phase contrast image of the cell aggregate containing a ciliary marginal zone-like structure (A, right row, upper panel), and a GFP fluorescence image of Crx gene-expressing cells of the cell aggregate containing a ciliary marginal zone-like structure (A, right row, lower panel) are shown. In the GFP fluorescence image of Crx gene-expressing cell in a cell aggregate containing a ciliary marginal zone-like structure (A, right row, lower panel), a continuous neural retina having a layer structure was found to exist adjacent to the ciliary marginal zone-like structure in the lower right part (shown by arrow).

The proportion of cell aggregates containing a continuous neural retina having a layer structure in not less than 10% of the cell aggregate circumference, in the cell aggregates without a ciliary marginal zone-like structure (CMZ−) and the cell aggregates with a ciliary marginal zone-like structure (CMZ+) was measured by using the morphology of the Crx gene-expressing cell as an index (FIG. 12B). As a result, it was found that the cell aggregate with a ciliary marginal zone-like structure (CMZ+) has a higher ratio of cell aggregates containing a continuous neural retina having a layer structure, as compared to the cell aggregates without a ciliary marginal zone-like structure (CMZ−).

INDUSTRIAL APPLICABILITY

According to the production method of the present invention, a ciliary marginal zone-like structure can be produced with high efficiency. In a cell aggregate comprising a ciliary marginal zone-like structure, which is produced by the production method of the present invention, the ciliary marginal zone-like structure functions as a progress zone, and a continuous neural retina having a layer structure can be formed adjacent to the ciliary marginal zone-like structure with high frequency.

This application is based on patent application No. 2012-130521 filed in Japan (filing date: Jun. 8, 2012), the contents of which are incorporated in full herein. All publications, patents and patent publications cited in the Specification are hereby incorporated by reference.

The invention claimed is:

1. A method for formation of a ciliary marginal zone-like structure in a retinal tissue derived from a cell aggregate comprising
   (a) preparing a cell aggregate from a pluripotent stem cell,
   (b) culturing the cell aggregate to form a retinal tissue comprising at least 20% of cells positive for Chx 10,
   (c) culturing the retinal tissue comprising at least 20% of cells positive for Chx10 in a serum-free medium containing a substance that enhances signal transduction mediated by Wnt for a period before the appearance of RPE65 expressing cells, thereby obtaining retinal tissue having a decreased proportion of Chx10 positive cells that is about 3% or less of the tissue,
   (d) culturing the retinal tissue with the decreased proportion of Chx10 positive cells of step (c) without the substance that enhances signal transduction mediated by Wnt in a serum-free medium containing a serum replacement or a serum-containing medium to induce the formation of a ciliary marginal zone-like structure in the retinal tissue, and
   (e) obtaining the retinal tissue having the ciliary marginal zone-like structure, wherein the ciliary marginal zone-like structure comprises Rdh10 positive cells.

2. The method according to claim 1, wherein the decreased proportion of Chx10 positive cells in step (c) is within 3% to 1% of the tissue.

3. The method according to claim 2, wherein the culturing in step (d) is until the proportion of Chx10 positive cells present in the retinal tissue reaches 50% or more of the tissue.

4. The method according to claim 1, wherein the pluripotent stem cell is a human pluripotent stem cell.

5. The method according to claim 1, wherein the culturing of the retinal tissue with the decreased proportion of Chx10 positive cells in step (d) is in a serum-free medium containing a serum replacement.

6. The method according to claim 1, wherein the culturing of the retinal tissue with the decreased proportion of Chx10 positive cells in step (d) is in a serum-containing medium.

7. The method according to claim 1, wherein the decreased proportion of Chx10 positive cells in step (c) is about 3% of the tissue.

8. The method according to claim 1, wherein the culturing of the cell aggregate in step (b) is to form a retinal tissue comprising at least 40% of cells positive for Chx10, and the culturing in step (c) is culturing the retinal tissue comprising at least 40% of cells positive for Chx10.

9. The method according to claim 1, wherein the culturing of the retinal tissue in step (c) is for 2 to 5 days.

10. The method according to claim 9, wherein the culturing of the retinal tissue in step (c) is for 2 to 3 days.

11. The method according to claim 1, wherein the culturing of the cell aggregate in step (b) is to form a retinal tissue comprising at least 40% of cells positive for Chx10, and the culturing in step (c) is culturing the retinal tissue comprising at least 40% of cells positive for Chx10 for 2 to 5 days.

12. A method for producing a neural retina comprising
(a) preparing a cell aggregate from a pluripotent stem cell,
(b) culturing the cell aggregate to form a retinal tissue comprising at least 20% of cells positive for Chx10,
(c) culturing the retinal tissue comprising at least 20% of cells positive for Chx10 in a serum-free medium containing a substance that enhances signal transduction mediated by Wnt for a period before appearance of RPE65 expressing cells, thereby obtaining retinal tissue having a decreased proportion of Chx10 positive cells that is about 3% or less of the tissue,
(d) culturing the retinal tissue with the decreased proportion of Chx10 positive cells of step (c) without the substance that enhances signal transduction mediated by Wnt in serum-free medium containing a serum replacement or a serum-containing medium to induce formation of a ciliary marginal zone-like structure in the retinal tissue,
(e) obtaining the retinal tissue having the ciliary marginal zone-like structure, wherein the ciliary marginal zone-like structure comprises Rdh10 positive cells, and a retinal pigment epithelium and a neural retina are present adjacent to the ciliary marginal zone-like structure, and
(f) cutting out the neural retina from the retinal tissue in step (e), thereby obtaining a purified neural retina.

13. The method according to claim 12, wherein the culturing of the cell aggregate in step (b) is to form a retinal tissue comprising at least 40% of cells positive for Chx10, and the culturing in step (c) is culturing the retinal tissue comprising at least 40% of cells positive for Chx10.

14. The method according to claim 12, wherein the culturing of the retinal tissue in step (c) is for 2 to 5 days.

15. The method according to claim 12, wherein the culturing of the cell aggregate in step (b) is to form a retinal tissue comprising at least 40% of cells positive for Chx10, and the culturing in step (c) is culturing the retinal tissue comprising at least 40% of cells positive for Chx10 for 2 to 5 days.

* * * * *